United States Patent [19]

Goldberg et al.

[11] Patent Number: 4,559,493
[45] Date of Patent: Dec. 17, 1985

[54] METER FOR MEASURING THE CONCENTRATION OF WATER IN A WATER-INK MIXTURE

[75] Inventors: Ira B. Goldberg; Kwang E. Chung, both of Thousand Oaks, Calif.; Thomas A. Fadner, Oshkosh, Wis.

[73] Assignee: Rockwell International Corporation, El Segundo, Calif.

[21] Appl. No.: 616,106

[22] Filed: Jun. 1, 1984

[51] Int. Cl.[4] .............................................. G01N 27/22
[52] U.S. Cl. .................. 324/61 R; 73/61.1 R
[58] Field of Search .................. 324/61 R; 73/61.1 R, 73/53

[56] References Cited

U.S. PATENT DOCUMENTS

| | | | |
|---|---|---|---|
| 3,739,266 | 6/1973 | Neitzel et al. | 324/61 R |
| 4,112,744 | 9/1978 | Tassano | 73/61.1 R |
| 4,130,796 | 12/1978 | Shum | 324/61 R |
| 4,399,404 | 8/1983 | Resh | 324/61 R |
| 4,429,273 | 1/1984 | Mazzagatti | 73/61.1 R X |

Primary Examiner—Stewart J. Levy
Assistant Examiner—Joseph W. Roskos
Attorney, Agent, or Firm—H. Fredrick Hamann; Craig O. Malin

[57] ABSTRACT

A meter is provided which can continuously measure the amount of water in a flowing mixture of water and lithographic ink. The mixture flows between the plates of a capacitor cell. This cell provides capacitance for an audio frequency oscillator. The output frequency of the oscillator is converted to a voltage which is proportional to the output frequency of the oscillator. This voltage is converted to a second voltage which is proportional to the logarithm of the first mentioned voltage and is also proportional to the concentration of water in the mixture. This second voltage is read out in a display device which can be set to read the water content of the mixture of water and ink.

7 Claims, 4 Drawing Figures

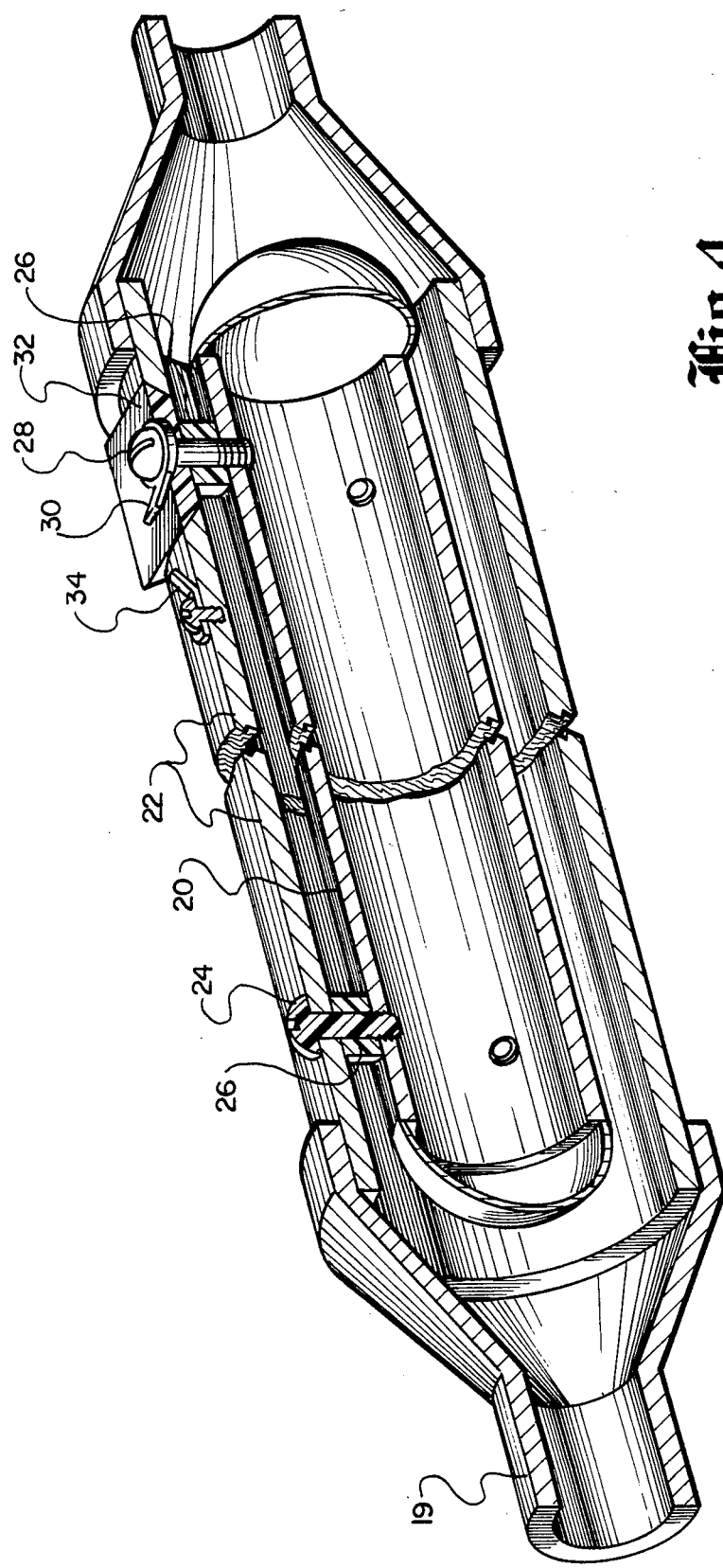

METER FOR MEASURING THE CONCENTRATION OF WATER IN A WATER-INK MIXTURE

BACKGROUND OF THE INVENTION

This invention relates to the field of meters and particularly to the field of meters for measuring the concentration of water in a water-ink mixture.

Lithographic printing presses use a mixture of ink and aqueous dampening solution. The dampening solution is water with small amounts of proprietary additives to enhance water wetting of the printing plate. A continuous flow of ink and of dampening solution are furnished to the press. These can be supplied as a mixture of ink and dampening solution; or as separate streams of ink and dampening solution depending upon press configuration. In any case, the useful printing mixture on press contains both ink and water. In keyless inking systems, for economical operation, the ink-water mixture could be recirculated, since only a fraction of the ink mixture is being consumed by the printing process at any given time.

In order to obtain the best printing results, the proper amounts of water and of ink in the mixture must be maintained. This can be done at start-up when a fresh water-ink mixture is added by using the proper proportions for making the mixture. However, over a period of time during printing the proportions of ink and water can change in the recirculating mixture. At present, the printer attending the press has no means of automatically and continuously monitoring the concentration of water in a recirculating water-ink mixture. He must rely upon his experience and the printing results to estimate the concentration of the water in the mixture.

Meters are known which measure the dielectric constant of a mixture to determine the moisture content of materials or the density of a mixture. Some of these prior art meters use a Wheatstone bridge-type circuit to measure dielectric properties (e.g., U.S. Pat. No. 3,696,299). Other use two oscillators to obtain a frequency differential which is related to the dielectric properties of the material being tested (e.g., U.S. Pat. No. 4,048,844). Still other meters use an oscillator with peak detectors (e.g., U.S. Pat. No. 4,399,404) or a logic circuit (e.g., U.S. Pat. No. 4,130,796). However, what the printer needs is a simple meter which will automatically provide a direct reading of the concentration of water in the ink.

SUMMARY OF THE INVENTION

It is an object of the invention to provide a meter for conveniently measuring the concentration of water in a mixture of water and ink.

According to the invention, the mixture to be measured forms the dielectric between the plates of a capacitor in a special capacitor cell. The cell provides capacitance for an audio frequency oscillator. When the dielectric constant of the mixture changes due to changes in the water content of the mixture, the output frequency of the oscillator changes. The output frequency of the oscillator is converted to a voltage which is proportional to the output frequency of the oscillator. This voltage is then converted to a second voltage which is proportional to the logarithm of the first mentioned voltage. This second voltage is read out in a display device. Because the concentration of water in water-ink mixtures is proportional to the logarithm of the mixtures dielectric constant, the display device can be set to provide a direct reading of the ratio of water in the water-ink mixture.

In a preferred embodiment, the special capacitor has an inlet and an outlet and is coupled in series by appropriate tubing to a recirculating water-ink mixture system at the press. The meter can then provide a continuous reading of the water in the mixture.

These and other objects and features of the invention will be apparent from the following detailed description taken together with reference to the accompanying drawings.

BRIEF DESCRIPTION OF THE DRAWINGS

FIG. 4 is a preferred embodiment of a capacitor cell for use in the invention.

DESCRIPTION OF THE PREFERRED EMBODIMENT

A microwave cavity was used to study the dielectric properties and the microwave absorption of water and lithographic ink mixtures. During these studies it was discovered that the logarithm of the real component, $\epsilon'$, of the dielectric constant, $\epsilon = \epsilon' + i\epsilon''$, is linear with the concentration of water in the water-ink mixture. This relationship is defined by the following equation:

$$\log \epsilon = \log \epsilon_0' + kC,$$

where $\epsilon'$ is the real part of the complex dielectric constant $\epsilon$ (shown above), $\epsilon_0'$ is its value for ink without added water, C is the concentration by weight of water (or water with dampening solution), and k is a proportionality constant.

Figure 1:
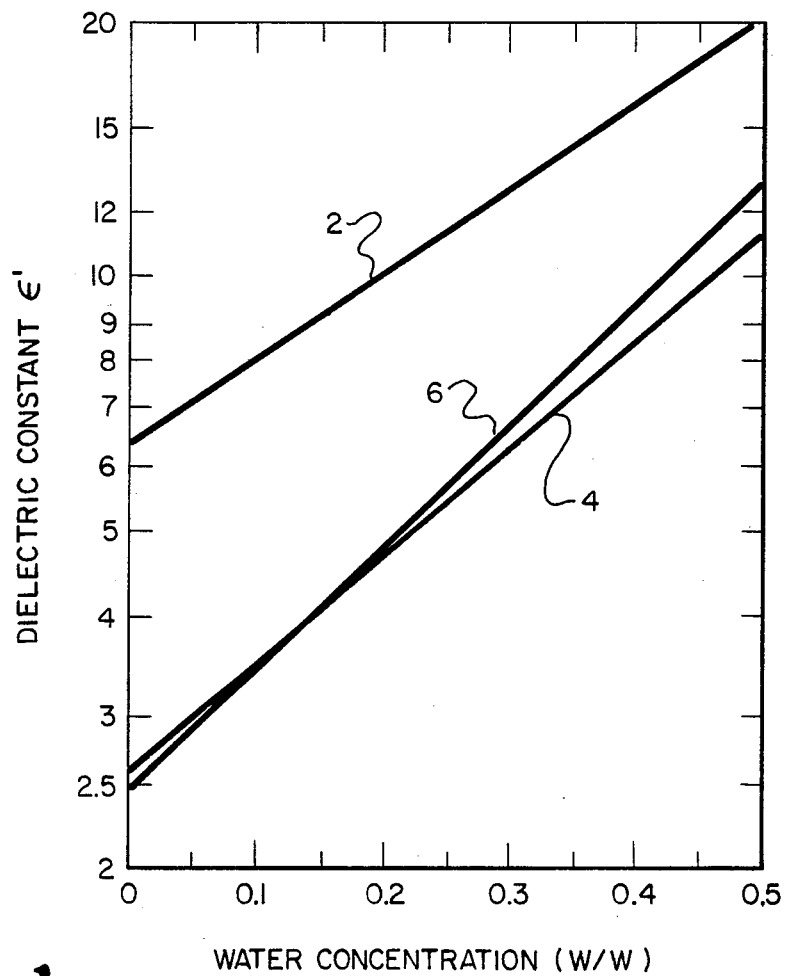
FIG. 1 is a graph showing the relationship between the water concentration (on a liner scale) and the dielectric constant (on a logarithmic scale) for water-ink mixtures of three different types of inks.

Additional testing showed that this relationship was reproducible, and that it applied to many different types of lithographic ink. FIG. 1 shows this logarithmic relationship for three different newspaper inks supplied by the Flint Ink Co., Detroit, MI, namely a black ink, curve 2, a yellow ink, curve 4, and a magenta ink, curve 6. These curves were obtained on mixtures tested at 23 degrees C. Testing at temperatures ranging from 10 degrees C. to 40 degrees C showed that the ink-water mixtures had an anomalously small temperature dependence. These results were surprising because water itself shows a large temperature dependence. Apparently, this anomalous behavior is related to the microstructure of the water-ink emulsion. In any event, the small temperature dependence and the reproducible phenomenological behavior (FIG. 1) provides a theoretical basis for a meter to measure the water concentration of water-ink mixtures as described below.

Figure 2:
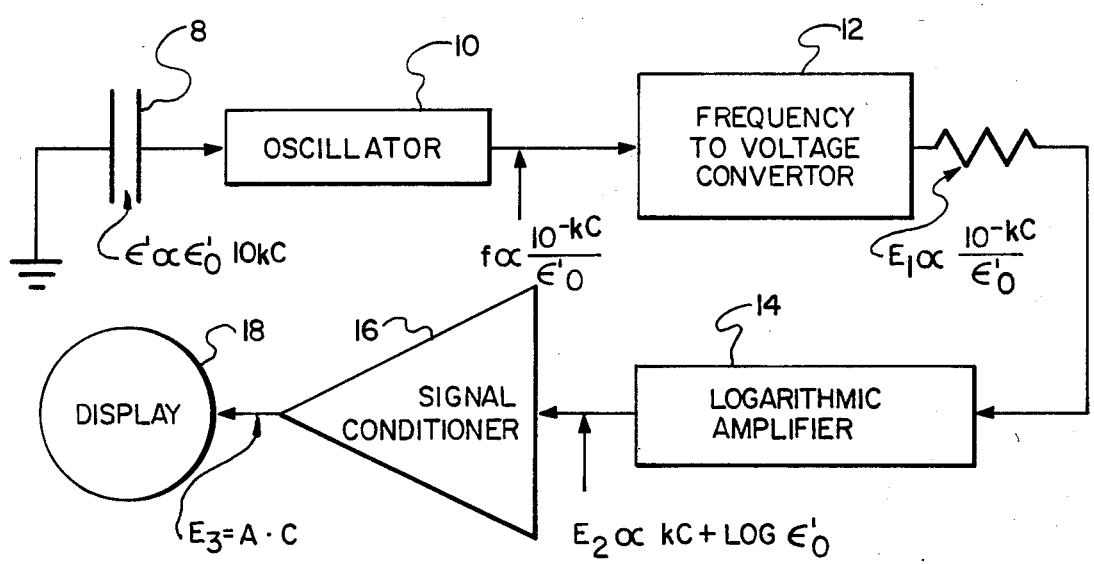
FIG. 2 is a block diagram of the ink meter circuit according to the invention.

FIG. 2 is a block diagram of a capacitance type meter according to the invention for obtaining a linear readout of the concentration, C, of water (or dampening solution) in an ink-water mixture. In this meter, the mixture acts as a dielectric material for a capacitor 8. The capacitance of capacitor 8 depends upon the dielectric constant $\epsilon'$ of the mixture and (as discussed above and as shown in FIG. 1) this in turn depends upon the concentration, C, of water in the mixture.

Capacitor cell 8 is a part of the circuit of an audio-frequency oscillator 10. Oscillator 10 provides a square wave frequency, f, which is inversely proportional to the dielectric constant of the mixture in capacitor 8. This is expressed by the equation:

$$f = \frac{1}{2R_fC_0\epsilon'} \cdot \frac{1}{\ln[(1+\beta)/(1-\beta)]},$$

where $R_f$ is the feedback resistor defined by the type of ink being measured, $\beta$ is the value of the resistance of the positive feedback loop of the oscillator, and $C_0$ is the capacitance of cell 8 in the absence of the mixture.

Once the square wave signal, f, is generated, a frequency-to-voltage converter 12 is used to convert the signal to a voltage, E, which is proportional to $10^{-kC/\epsilon_0'}$. As shown in FIG. 1, the logarithm of the dielectric constant, is linear with the concentration of fountain solution, C. Therefore, $E_1$ is converted to base 10 logarithm by logarithm amplifier 14. Because a limited logarithmic range is required, unit 14 can be constructed from an inexpensive operational amplifier and an appropriate NPN transistor, or can be purchased as a modular unit as shown later in the schematic diagram. In fact, at low concentration of water (e.g., 0-20% water), the relationship between water concentration and dielectric constant $\epsilon'$ is sufficiently linear to provide an accuracy of ±1% without a logarithmic amplifier. Consequently, for meters used only for measuring concentrations less than about 20% water, logarithmic amplifier 14 can be eliminated, The output voltage, $E_2$, is proportional to the concentration of water, C, offset by some arbitrary voltage as shown by the relationship: $E_2 \propto kC + \log \epsilon_0'$. Log $\epsilon_0'$ is a constant for the particular type of ink being tested.

The final stage of the water-ink mixture meter is an amplifier 16 for conditioning the signal from logarithmic amplifier 14 and a display device 18 for reading out the signal. Amplifier 16 has an adjustable offset voltage and an adjustable gain from 0.95 to 20 in order to provide a voltage output of 0 volts when the concentration of water in the water-ink mixture is 0 (C=0) and 5 volts when its concentration is 50% (C=50%).

Figure 3:
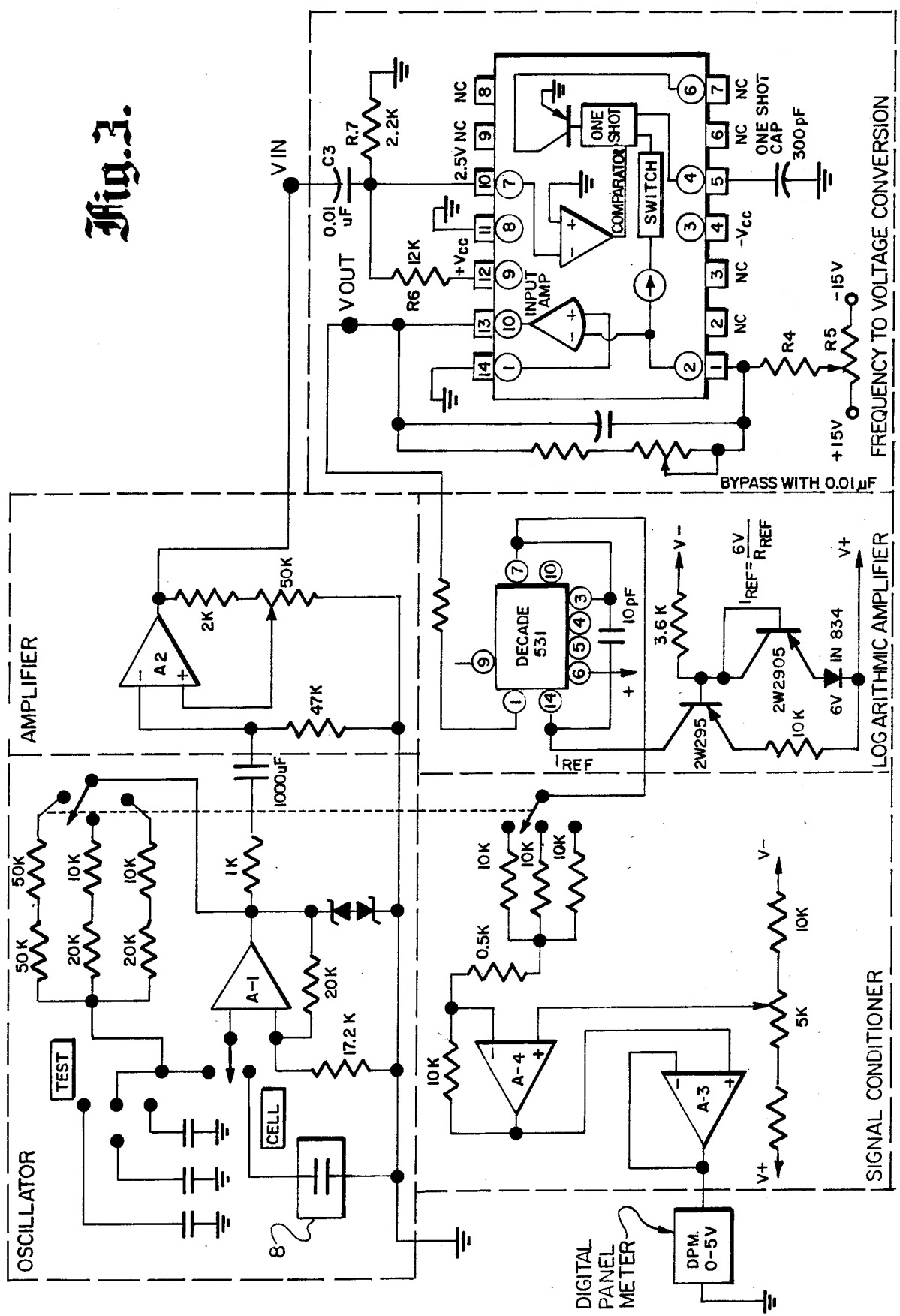
FIG. 3 is a schematic diagram of the ink meter circuit according to the invention.

A functional schematic diagram of the meter is shown in FIG. 3. The unit consists of an oscillator (multivibrator) which uses amplifier A1 shown at the upper left hand corner. A three position switch is used to select the appropriate feedback capacitors to set the frequency based on some reference point (e.g., empty cell or known ink-water system). The output from the oscillator is amplified (Amplifier A2) by an amount determined by the positive gain setting, (50+2)/x where x is the resistance between the wiper of the 50 kΩ potentiometer and ground (in kΩ). This is a noncritical setting and is needed only to ensure that there is a proper signal amplitude to trigger the frequency-to-voltage converter (Burr-Brown VF32) shown in the lower right corner of the figure. This integrated circuit provides a voltage directly proportional to the frequency. A reference voltage to input 1 provides a reference voltage for the logarithmic zero point.

This constant voltage is then fed into a logarithmic amplifier (Burr-Brown Log 100 module) shown at the bottom center of FIG. 3. This is connected such that a 3-decade span per 10 V is maintained. A reference current to pin 14 is supplied by a simple current regulated circuit shown below the log-amplifier. The output of the unit is positive above a 1 V (input (log 1=0), and is inverted with the 0 to −1 gain amplifier A4. The gain settings are switched with the appropriate feedback resistors for the multivibrator circuit as shown by the dotted line. This amplifier serves two functions. The first is to establish the proportionally constant K using the appropriate gain settings as described in the previous section, and the second is to establish the zero point voltage to correct for log $\epsilon_0'$.

The output of A4 is fed into A3 which acts as a buffer for the digital panel meter DM 3100L set for a 0 to 5 volt output. The unit can be adjusted, for instance, to read 1 volt for 10% water concentration. The four amplifiers (A1 to A4) shown in FIG. 3 can be combined into a "quad op-amp" integrated circuit such as National Semiconductor LF 457.

With nominal modification the circuit can be adjusted to operate at any frequency which responds linearly to the dielectric constant of the ink. Frequencies which have been used for various inks range from less than 3 kHz to over 300 kHz. However, care should be taken in constructing the meter to minimize stray capacitance and to use an amplifier with a sufficient gain-bandwidth product and a negligible phase shift below 3 MHz.

FIG. 4 shows the design of a capacitor cell 8 for use in the meter of the invention. This cell may be designed so that it can be placed in series with, for instance, a ¾ inch diameter pipe 19 carrying the water-ink mixture of a large printing press. The inner member 20 is supported within an outer member 22 and electrically isolated from it by, for instance, nylon screws 24 and nylon spacers 26. Inner member 20 is a tube with closed ends, and it serves as one of the plates of capacitor 8. Oscillator 10 is connected to inner member 20 by metal screw 28 and connector 30. It is insulated from outer member 22 by spacer 26 and insulating bushing 32.

Outer member 22 serves as the other plate of capacitor cell 8. It is electrically connected to oscillator 10 through connector 34. In this design a space of about 0.2 inch in provided for the flowing water ink mixture which, as such, becomes the dielectric of the capacitor cell.

The facing surfaces of members 22 and 20 are coated with a thin (0.005–0.010 inch) non-conducting polymeric layer (e.g., teflon or polyvinyl chloride) to eliminate electrolytic conductance and to prevent corrosion.

Numerous variations and modifications can be made without departing from the invention. For example, the capacitor cell 8 can be designed as a pair of flat parallel plates rather than the concentric tube design illustrated in FIG. 4. The mixture being measured can include inks other than lithographic inks if the relation between the dielectric constant and the water concentration of the mixture is similar to that for mixtures containing lithographic inks. The measurements can be made of a flowing stream or simply of a batch of mixture. Accordingly, it should be understood that the specific form of the invention described above is illustrative only and is not intended to limit the scope of the invention.

What is claimed is:

1. A meter for measuring the concentration of water in a fluid mixture of ink and water, said meter comprising:
   a capacitor cell for containing a fluid mixture;
   an audio-frequency oscillator circuit which utilizes said capacitor cell for providing capacitance in said oscillator circuit so that said oscillator circuit provides an output frequency which is inversely proportional to the dielectric constant of said fluid;

a frequency to voltage converter which receives said output frequency of said oscillator circuit and converts it to a first voltage output which is directly proportional to said output frequency;

a logarithmic amplifier which receives said first voltage output of said frequency-voltage converter and converts it to a second voltage output which is proportional to the logarithm of said first voltage output and is directly proportional to said concentration of water in said fluid mixture in said capacitor cell; and a display means which receives said second voltage output of said logarithmic amplifier and displays it, whereby said concentration of water in said fluid mixture in said capacitor cell can be measured.

2. The meter as claimed in claim 1, wherein said fluid mixture is a flowing fluid mixture and said capacitor cell has an inlet and an outlet for receiving and discharging said flowing fluid mixture.

3. The meter as claimed in claim 1 including a first amplifier between said oscillator circuit and said frequency to voltage converter to provide a signal of proper amplitude for said frequency to voltage converter.

4. The meter as claimed in claim 1 including a second amplifier to receive the output from said logarithmic amplifier and establish the proper zero point voltage for the mixture being measured and a third amplifier to receive the output of said second amplifier and serve as a buffer for said display means.

5. The meter as claimed in claim 1, wherein said oscillator circuit includes selectable resistance and capacitance means to select an appropriate feedback to set the frequency for specific mixtures.

6. The meter as claimed in claim 2, wherein said capacitor cell comprises an inner closed-ended cylinder spaced concentrically within an outer open-ended cylinder, and separate electrical connectors to said inner and to said outer cylinders, the space between said concentrically spaced cylinders being provided to contain said flowing fluid mixture.

7. A meter for measuring the concentration of water in a flowing fluid mixture of ink and water, said meter comprising:

a capacitor cell having an inlet and an outlet for receiving and discharging a fluid mixture;

an audio-frequency oscillator circuit which utilizes said capacitor cell for providing capacitance in said oscillator circuit so that said oscillator circuit provides an output frequency which is inversely proportional to the dielectric constant of said fluid, said oscillator circuit having selectable resistance and capacitance means to select an appropriate feedback to set the frequency for specific mixtures;

a first amplifier for amplifying the output of said oscillator circuit;

a frequency to voltage converter which receives sand amplified output frequency of said oscillator circuit and converts it tod a first voltage output which is directly proportional to said output frequency;

a logarithmic amplifier which receives said first voltage output of said frequency-voltage converter and converts it to a second voltage output which is proportional to the logarithm of said first voltage output and is directly proportional to said concentration of water in said fluid mixture in said capacitor cell;

a second amplifier which receives the output from said logarithmic amplifier and establishes the proper zero point voltage for the mixture being measured;

a buffer amplifier which receives the output of said second amplifier; and a display means which receives the output of said buffer amplifier and displays it, whereby said concentration of water in said fluid mixture in said capacitor cell can be measured.

* * * * *